(12) United States Patent
Pinter

(10) Patent No.: US 8,475,799 B2
(45) Date of Patent: Jul. 2, 2013

(54) HIV-1 GP41 NEUTRALIZATION DOMAIN AND USE THEREOF

(75) Inventor: Abraham Pinter, Brooklyn, NY (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 435 days.

(21) Appl. No.: 12/672,585

(22) PCT Filed: Aug. 11, 2008

(86) PCT No.: PCT/US2008/072764
§ 371 (c)(1),
(2), (4) Date: Sep. 3, 2010

(87) PCT Pub. No.: WO2009/021230
PCT Pub. Date: Feb. 12, 2009

(65) Prior Publication Data
US 2011/0091491 A1    Apr. 21, 2011

Related U.S. Application Data

(60) Provisional application No. 60/954,862, filed on Aug. 9, 2007.

(51) Int. Cl.
*A61K 39/42* (2006.01)
*A61K 39/21* (2006.01)
*C07K 16/00* (2006.01)

(52) U.S. Cl.
USPC ................ 424/160.1; 424/208.1; 530/388.35

(58) Field of Classification Search
None
See application file for complete search history.

(56) References Cited

U.S. PATENT DOCUMENTS 7,311,916 B2 * 12/2007 Wild et al. ................ 424/188.1
2004/0213801 A1  10/2004 Wild et al. ................ 424/188.1

FOREIGN PATENT DOCUMENTS

WO   WO 2005/111621   11/2005

OTHER PUBLICATIONS

Zwick, M. B., et al., Nov. 2001, Broadly neutralizing antibodies targeted to the membrane-proximal external region of human immunodeficiency virus type 1 glycoprotein gp41, J. Virol. 75(22):10892-10905.*
Forthal, D. N., et al., 1995, Functional activities of 20 human immunodeficiency virus type 1 (HIV-1)-specific human monoclonal antibodies, AIDS Res. Human Retrovir. 11(9):1095-1099.*
Corti, D., et al., Jan. 2010, Analysis of memory B cell responses and isolation of novel monoclonal antibodies with neutralizing breadth from HIV-1-infected individuals, PLoS One 5(1):e8805:1-15.*
Watkins, B. A., et al., 1996, Resistance of human immunodeficiency virus type 1 to neutralization by natural antissera occurs through single amino acid substitutions that cause changes in antibody binding at multiple sites, J. Virol. 70(12):8431-8437.*
Alam et al. "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes" The Journal of Immunology 2007 vol. 178: 4424-4435.
Conley et al. "Neutralization of Divergent Human Immunodeficiency Virus Type 1 Variants and Primary Isolates by IAM-41-2F5, an Anti-gp41 Human Monoclonal Antibody" Proc. Natl. Acad. Sci. USA 1994 vol. 91:3348-3352.
Conley et al. UniProtKB 1996 accession No. Q69910.
Gorny, M.K. and Zolla-Pazner, S. "Human Monoclonal Antibodies that Neutralize HIV-1" HIV Databases Review Article 2003 in HIV Immunology and HIV/SIV Vaccine Databases Los Alamos National Laboratory, Theoretical Biology and Biophysics, Los Alamos, New Mexico LA-UR 04-8162: 1-19.
HIV Molecular Immunology 2002 Los Alamos National Laboratory, Theoretical Biology and Biophysics, Los Alamos, New Mexico LA-DR 03-5816.
HIV Immunology and HIV/SIV Vaccine Database 2003 http://www.hiv.lanl.gov/content/immunology/contents2003 .html.

* cited by examiner

*Primary Examiner* — Jeffrey Parkin
(74) *Attorney, Agent, or Firm* — Licata & Tyrrell P.C.

(57) ABSTRACT

The invention relates to isolated monoclonal antibodies which specifically bind to the C-terminal heptad repeat region of gp41 (HR2) and neutralize an HIV-1 primary isolate.

3 Claims, 6 Drawing Sheets

N-TERMINAL GP120 (V1/V2) EXCHANGES

| Plasmid | Structure | 53M SERUM DILUTIONS FOR 50% NEUTRAL. |
|---|---|---|
| p163 | V1/V2 – V3 V3 – V4 – V5 – gp41 | 16,000 |
| p1661 | V1/V2 – V3 V3 – V4 – V5 – gp41 | 6,800 |
| p1665 | V1/V2 – V3 V3 – V4 – V5 – gp41 | 15,000 |
| p1664 | V1/V2 – V3 V3 – V4 – V5 – gp41 | 3,500 |
| p1662 | V1/V2 – V3 V3 – V4 – V5 – gp41 | 550 |
| p166 | V1/V2 – V3 V3 – V4 – V5 – gp41 | << 100 |

Restriction sites: BglII, PpuM I, PmlI, MfeI

C-TERMINAL GP120 (V3-V5) DOMAIN EXCHANGES

| Plasmid | Structure | 53M SERUM DILUTIONS |
|---|---|---|
| p163 | V1/V2 – V3 V3 – V4 – V5 – gp41 | 16,000 |
| p1663 | V1/V2 – V3 V3 – V4 – V5 – gp41 | 2,900 |
| p1661 | V1/V2 – V3 V3 – V4 – V5 – gp41 | 6,800 |
| p1666 | V1/V2 – V3 V3 – V4 – V5 – gp41 | 1,650 |

GP41 EXCHANGES

| Plasmid | Structure | 53M SERUM DILUTIONS |
|---|---|---|
| p1663 | V1/V2 – V3 V3 – V4 – V5 – gp41 | 2,900 |
| p1662 | V1/V2 – V3 V3 – V4 – V5 – gp41 | 550 |
| p1666 | V1/V2 – V3 V3 – V4 – V5 – gp41 | 1,650 |
| p166 | V1/V2 – V3 V3 – V4 – V5 – gp41 | << 100 |

Legend: ☐ 53M   ▨ 133M

*FIG. 1*

```
              513    gp41 FUSION PEP   |              |
    C1    AV  GIGAVFLGFLGAAGSTMGAA  SITLTVQARQLLSGIVQQQS
    C2    AV  GIGAVLLGFLGAAGSTMGAA  SITLTAQARQVLSGIVQQQS
    C3    AV  GLGAMFLGFLGAAGSTMGAA  SITLTVQARQLLSGIVQQQN
    C4    AV  GIGAVFLGFLGAAGSTMGAA  SITLTVQARQLLSGIVQQQS
    C5    AV  GIGAVFLGFLGVAGSTMGAA  SITLTAQARQVLSGIVQQQS
    C6    AV  GIGAVFLGFLGAAGSTMGAA  SITLTVQARQLLSGIVQQQS
    P1531 AV  TLGAMFLGFLGAAGSTMGAA  SLTLTVQARQLLSGIVQQQN

N-TERM HEPTAD REPEAT                    |  593
    C1    NLLRAIEAQQHMLQLTVWGI   KQLQTRVLAIERYLKDQQLL
    C2    NLLRAIEAQQHLLQLTVWGI   KQLQTRVLALERYLKDQQLL
    C3    NLLRAIEAQQHMLQLTVWGI   KQLQARVLAIERYLKDQQLL
    C4    NLLRAIEAQQHMLQLTVWGI   KQLQARVLAIERYLKDQQLL
    C5    NLLRAIEAQQHMLQLTVWGI   KQLQARVLAIERYLKDQQLL
    C6    NLLKAIEAQQHLLQLTVWGI   KQLQARVLAIERYLQDQQLL
    P1531 NLLRAIEAHQHLLHLTVWGI   KQLQARVLAVERYLKDQQLL

594                               |
    C1    GIWGCSGKLICTTAVPWNTS  WSNKSVTDIWDNMTWMQWDK
    C2    GLWGCSGRLICTTAVPWNSS  WSNKSLTDIWDNMTWMQWDK
    C3    GLWGCSGKLVCTTAVPWNSS  WSNKSQEDIWNNTTWMQWDK
    C4    GIWGCSGKLICTTNVPWNSS  WSNKSLGDIWDNMTWMEWDR
    C5    GIWGCSGKLICTTAVPWEDS  WSNRTQEEIWNNMTWMQWDK
    C6    GIWGCSGKLICTTAVPWNSS  WSNKSKEEIWGNMTWMQWDK
    P1531 GIWGCSGKLICTTAVPWNAS  WSNKSLDQIWNNMTWMEWER

C-TERM HEPTAD REPEATS          |
    C1    EISNYTNTIYRLLEDSQNQQ  EKNEKDLLALDSWKNLWNWF
    C2    EVSNYTNTIYRLLEDSQSQQ  EKNEKDLLALDSWKNLWTWF
    C3    EVSNYTKTIYKLLEKSQNQQ  EENEKDLLALDSWLNLWNWF
    C4    EISNYTNIIFGLLEDSQNQQ  ERNEKDLLALDKWNNLWNWF
    C5    EISNYTDTIYKLLTESQSQQ  DKNEKDLLALDSWKNLWNWF
    C6    EVSNYTFTIYQLLEESQYQQ  EQNEKELLALNKWNDLWSWF
    P1531 EIDNYTNLIYTLIEESQNQQ  EKNEQELLELDKWASLWNWF

693
    C1    DITNWLWYIKIFIMIVGGLI
    C2    DISNWLWYIKIFIMVVGGLI
    C3    DISNWLWYIKIFIMIVGGLI
    C4    NITQWLWYIKIFIMIVGGLI
    C5    DITQWLWYIRIFIMIVGGLI
    C6    NITNWLWYIKIFIMIVGGLI
    P1531 DISKWLWYIKIFIMIVGGLV
```

*FIG. 2*

ALL MUTATIONS ARE IN p1666 BACKGROUND

```
p1666  | Ź | V1/V2 | Ź | V3 | V3' | V4 | V5 |    gp41    |
       |   133M    |    53M    |
```

```
                         616 619    627
                          |   |      |              IC50
p1666 (133M/53M gp41)   NYTKTIYKLLEKSQNQQEE        1,800
p1689 (K619N)           ---N---------------          160
p1692 K619N/K627D)      ---N-------D-------         <100
p1688 (N616Q)           Q------------------        1,500
133M wt                 ---N---R---D-------         <100

HXB2                    NYTSLIHSLIEESQNQQEK
                         |                 |
                        637               656
                        (HXB2 NUMBERING SYSTEM)
```

```
                              *    **   *  **
53MPB21        DKEISNYTKTIYKLLEKSQNQQEENEKD
135MPL23a      DKEISNYTDTIYKLLTESQSQQDKNEKD

135(K/EK/N)    DKEISNYTKTIYKLLEKSQNQQDKNEKD

CLADE C CONS   DREISNYTDTIYRLLEDSQNQQEKNEKD
CLADE B CONS   EREIDNYTgLIYTLIEESQNQQEKNEQE
```

```
                       *   *   *      *
53MP          EVSNYTKTIYKLLEKSQNQQEENEKD
133M          EISNYTNTIYRLLEDSQNQQEKNEKD
106F          EVSNYTNTIYRLLEDSQSQQEKNEKD
55F           EISNYTNIIFGLLEDSQNQQERNEKD
135MPL23a     EISNYTDTIYKLLTESQTQQDKNEKD
109F          EVSNYTFTIYQLLEESQYQQEQNEKD

CLADE C CONS  EISNYTDTIYRLLEDSQNQQEKNEKD
CLADE B CONS  EIDNYTgLIYTLIEESQNQQEKNEQE
```

FIG. 8

```
                        SEQUENCE LISTING

<160> NUMBER OF SEQ ID NOS: 52

<210> SEQ ID NO 1
<211> LENGTH: 36
<212> TYPE: PRT
<213> ORGANISM: Artificial sequence
<220> FEATURE:
<223> OTHER INFORMATION: Synthetic peptide

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 20
<212> TYPE: PRT
<213> ORGANISM: Human immunodeficiency virus

<400> SEQUENCE: 2

Ser Leu Ile Glu Glu Ser Gln Asn Gln Gln Glu Lys Asn Glu Gln Glu
1               5                   10                  15

Leu Leu Glu Leu
            20

<210> SEQ ID NO 3
<211> LENGTH: 182
<212> TYPE: PRT
<213> ORGANISM: Human immunodeficiency virus

<400> SEQUENCE: 3

Ala Val Thr Leu Gly Ala Met Phe Leu Gly Phe Leu Gly Ala Ala Gly
1               5                   10                  15

Ser Thr Met Gly Ala Ala Ser Leu Thr Leu Thr Val Gln Ala Arg Gln
            20                  25                  30

Leu Leu Ser Gly Ile Val Gln Gln Gln Asn Asn Leu Leu Arg Ala Ile
        35                  40                  45
```

```
Glu Ala His Gln His Leu Leu His Leu Thr Val Trp Gly Ile Lys Gln
 50                  55                  60

Leu Gln Ala Arg Val Leu Ala Val Glu Arg Tyr Leu Lys Asp Gln Gln
 65                  70                  75                  80

Leu Leu Gly Ile Trp Gly Cys Ser Gly Lys Leu Ile Cys Thr Thr Ala
                 85                  90                  95

Val Pro Trp Asn Ala Ser Trp Ser Asn Lys Ser Leu Asp Gln Ile Trp
                100                 105                 110

Asn Asn Met Thr Trp Met Glu Trp Glu Arg Glu Ile Asp Asn Tyr Thr
            115                 120                 125

Asn Leu Ile Tyr Thr Leu Ile Glu Glu Ser Gln Asn Gln Gln Glu Lys
        130                 135                 140

Asn Glu Gln Glu Leu Leu Glu Leu Asp Lys Trp Ala Ser Leu Trp Asn
145                 150                 155                 160

Trp Phe Asp Ile Ser Lys Trp Leu Trp Tyr Ile Lys Ile Phe Ile Met
                165                 170                 175

Ile Val Gly Gly Leu Val
            180

<210> SEQ ID NO 4
<211> LENGTH: 182
<212> TYPE: PRT
<213> ORGANISM: Human immunodeficiency virus

<400> SEQUENCE: 4

Ala Val Gly Ile Gly Ala Val Phe Leu Gly Phe Leu Gly Ala Ala Gly
 1               5                  10                  15

Ser Thr Met Gly Ala Ala Ser Ile Thr Leu Thr Val Gln Ala Arg Gln
                 20                  25                  30

Leu Leu Ser Gly Ile Val Gln Gln Gln Ser Asn Leu Leu Arg Ala Ile
         35                  40                  45

Glu Ala Gln Gln His Met Leu Gln Leu Thr Val Trp Gly Ile Lys Gln
 50                  55                  60

Leu Gln Thr Arg Val Leu Ala Ile Glu Arg Tyr Leu Lys Asp Gln Gln
 65                  70                  75                  80

Leu Leu Gly Ile Trp Gly Cys Ser Gly Lys Leu Ile Cys Thr Thr Ala
                 85                  90                  95

Val Pro Trp Asn Thr Ser Trp Ser Asn Lys Ser Val Thr Asp Ile Trp
                100                 105                 110

Asp Asn Met Thr Trp Met Gln Trp Asp Lys Glu Ile Ser Asn Tyr Thr
            115                 120                 125

Asn Thr Ile Tyr Arg Leu Leu Glu Asp Ser Gln Asn Gln Gln Glu Lys
        130                 135                 140

Asn Glu Lys Asp Leu Leu Ala Leu Asp Ser Trp Lys Asn Leu Trp Asn
145                 150                 155                 160

Trp Phe Asp Ile Thr Asn Trp Leu Trp Tyr Ile Lys Ile Phe Ile Met
                165                 170                 175

Ile Val Gly Gly Leu Ile
            180

<210> SEQ ID NO 5
<211> LENGTH: 182
<212> TYPE: PRT
<213> ORGANISM: Human immunodeficiency virus

<400> SEQUENCE: 5

Ala Val Gly Ile Gly Ala Val Leu Leu Gly Phe Leu Gly Ala Ala Gly
```

```
1               5                   10                  15
Ser Thr Met Gly Ala Ala Ser Ile Thr Leu Thr Ala Gln Ala Arg Gln
                20                  25                  30

Val Leu Ser Gly Ile Val Gln Gln Gln Ser Asn Leu Leu Arg Ala Ile
                35                  40                  45

Glu Ala Gln Gln His Leu Leu Gln Leu Thr Val Trp Gly Ile Lys Gln
            50                  55                  60

Leu Gln Thr Arg Val Leu Ala Leu Glu Arg Tyr Leu Lys Asp Gln Gln
65                  70                  75                  80

Leu Leu Gly Leu Trp Gly Cys Ser Gly Arg Leu Ile Cys Thr Thr Ala
                85                  90                  95

Val Pro Trp Asn Ser Ser Trp Ser Asn Lys Ser Leu Thr Asp Ile Trp
                100                 105                 110

Asp Asn Met Thr Trp Met Gln Trp Asp Lys Glu Val Ser Asn Tyr Thr
                115                 120                 125

Asn Thr Ile Tyr Arg Leu Leu Glu Asp Ser Gln Ser Gln Gln Glu Lys
                130                 135                 140

Asn Glu Lys Asp Leu Leu Ala Leu Asp Ser Trp Lys Asn Leu Trp Thr
145                 150                 155                 160

Trp Phe Asp Ile Ser Asn Trp Leu Trp Tyr Ile Lys Ile Phe Ile Met
                165                 170                 175

Val Val Gly Gly Leu Ile
                180

<210> SEQ ID NO 6
<211> LENGTH: 182
<212> TYPE: PRT
<213> ORGANISM: Human immunodeficiency virus

<400> SEQUENCE: 6

Ala Val Gly Leu Gly Ala Met Phe Leu Gly Phe Leu Gly Ala Ala Gly
1               5                   10                  15

Ser Thr Met Gly Ala Ala Ser Ile Thr Leu Thr Val Gln Ala Arg Gln
                20                  25                  30

Leu Leu Ser Gly Ile Val Gln Gln Gln Asn Asn Leu Leu Arg Ala Ile
                35                  40                  45

Glu Ala Gln Gln His Met Leu Gln Leu Thr Val Trp Gly Ile Lys Gln
            50                  55                  60

Leu Gln Ala Arg Val Leu Ala Ile Glu Arg Tyr Leu Lys Asp Gln Gln
65                  70                  75                  80

Leu Leu Gly Leu Trp Gly Cys Ser Gly Lys Leu Val Cys Thr Thr Ala
                85                  90                  95

Val Pro Trp Asn Ser Ser Trp Ser Asn Lys Ser Gln Glu Asp Ile Trp
                100                 105                 110

Asn Asn Thr Thr Trp Met Gln Trp Asp Lys Glu Val Ser Asn Tyr Thr
                115                 120                 125

Lys Thr Ile Tyr Lys Leu Leu Glu Lys Ser Gln Asn Gln Gln Glu Glu
                130                 135                 140

Asn Glu Lys Asp Leu Leu Ala Leu Asp Ser Trp Leu Asn Leu Trp Asn
145                 150                 155                 160

Trp Phe Asp Ile Ser Asn Trp Leu Trp Tyr Ile Lys Ile Phe Ile Met
                165                 170                 175

Ile Val Gly Gly Leu Ile
                180
```

```
<210> SEQ ID NO 7
<211> LENGTH: 182
<212> TYPE: PRT
<213> ORGANISM: Human immunodeficiency virus

<400> SEQUENCE: 7

Ala Val Gly Ile Gly Ala Val Phe Leu Gly Phe Leu Gly Ala Ala Gly
1               5                   10                  15

Ser Thr Met Gly Ala Ala Ser Ile Thr Leu Thr Val Gln Ala Arg Gln
            20                  25                  30

Leu Leu Ser Gly Ile Val Gln Gln Ser Asn Leu Leu Arg Ala Ile
        35                  40                  45

Glu Ala Gln Gln His Met Leu Gln Leu Thr Val Trp Gly Ile Lys Gln
50                  55                  60

Leu Gln Ala Arg Val Leu Ala Ile Glu Arg Tyr Leu Lys Asp Gln Gln
65                  70                  75                  80

Leu Leu Gly Ile Trp Gly Cys Ser Gly Lys Leu Ile Cys Thr Thr Asn
                85                  90                  95

Val Pro Trp Asn Ser Ser Trp Ser Asn Lys Ser Leu Gly Asp Ile Trp
            100                 105                 110

Asp Asn Met Thr Trp Met Glu Trp Asp Arg Glu Ile Ser Asn Tyr Thr
            115                 120                 125

Asn Ile Ile Phe Gly Leu Leu Glu Asp Ser Gln Asn Gln Gln Glu Arg
130                 135                 140

Asn Glu Lys Asp Leu Leu Ala Leu Asp Lys Trp Asn Asn Leu Trp Asn
145                 150                 155                 160

Trp Phe Asn Ile Thr Gln Trp Leu Trp Tyr Ile Lys Ile Phe Ile Met
                165                 170                 175

Ile Val Gly Gly Leu Ile
            180

<210> SEQ ID NO 8
<211> LENGTH: 182
<212> TYPE: PRT
<213> ORGANISM: Human immunodeficiency virus

<400> SEQUENCE: 8

Ala Val Gly Ile Gly Ala Val Phe Leu Gly Phe Leu Gly Val Ala Gly
1               5                   10                  15

Ser Thr Met Gly Ala Ala Ser Ile Thr Leu Thr Ala Gln Ala Arg Gln
            20                  25                  30

Val Leu Ser Gly Ile Val Gln Gln Gln Ser Asn Leu Leu Arg Ala Ile
        35                  40                  45

Glu Ala Gln Gln His Met Leu Gln Leu Thr Val Trp Gly Ile Lys Gln
50                  55                  60

Leu Gln Ala Arg Val Leu Ala Ile Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Glu Asp Ser Trp Ser Asn Arg Thr Gln Glu Glu Ile Trp
            100                 105                 110

Asn Asn Met Thr Trp Met Gln Trp Asp Lys Glu Ile Ser Asn Tyr Thr
            115                 120                 125

Asp Thr Ile Tyr Lys Leu Leu Thr Glu Ser Gln Ser Gln Gln Asp Lys
130                 135                 140

Asn Glu Lys Asp Leu Leu Ala Leu Asp Ser Trp Lys Asn Leu Trp Asn
145                 150                 155                 160
```

```
Trp Phe Asp Ile Thr Gln Trp Leu Trp Tyr Ile Arg Ile Phe Ile Met
                165                 170                 175

Ile Val Gly Gly Leu Ile
            180

<210> SEQ ID NO 9
<211> LENGTH: 182
<212> TYPE: PRT
<213> ORGANISM: Human immunodeficiency virus

<400> SEQUENCE: 9

Ala Val Gly Ile Gly Ala Val Phe Leu Gly Phe Leu Gly Ala Ala Gly
1               5                   10                  15

Ser Thr Met Gly Ala Ala Ser Ile Thr Leu Thr Val Gln Ala Arg Gln
            20                  25                  30

Leu Leu Ser Gly Ile Val Gln Gln Gln Ser Asn Leu Leu Lys Ala Ile
        35                  40                  45

Glu Ala Gln Gln His Leu Leu Gln Leu Thr Val Trp Gly Ile Lys Gln
    50                  55                  60

Leu Gln Ala Arg Val Leu Ala Ile Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ser Ser Trp Ser Asn Lys Ser Lys Glu Glu Ile Trp
            100                 105                 110

Gly Asn Met Thr Trp Met Gln Trp Asp Lys Glu Val Ser Asn Tyr Thr
        115                 120                 125

Phe Thr Ile Tyr Gln Leu Leu Glu Glu Ser Gln Tyr Gln Gln Glu Gln
    130                 135                 140

Asn Glu Lys Glu Leu Leu Ala Leu Asn Lys Trp Asn Asp Leu Trp Ser
145                 150                 155                 160

Trp Phe Asn Ile Thr Asn Trp Leu Trp Tyr Ile Lys Ile Phe Ile Met
                165                 170                 175

Ile Val Gly Gly Leu Ile
            180

<210> SEQ ID NO 10
<211> LENGTH: 19
<212> TYPE: PRT
<213> ORGANISM: Artificial sequence
<220> FEATURE:
<223> OTHER INFORMATION: Synthetic peptide

<400> SEQUENCE: 10

Asn Tyr Thr Lys Thr Ile Tyr Lys Leu Leu Glu Lys Ser Gln Asn Gln
1               5                   10                  15

Gln Glu Glu

<210> SEQ ID NO 11
<211> LENGTH: 19
<212> TYPE: PRT
<213> ORGANISM: Artificial sequence
<220> FEATURE:
<223> OTHER INFORMATION: Synthetic peptide

<400> SEQUENCE: 11

Asn Tyr Thr Ser Leu Ile His Ser Leu Ile Glu Glu Ser Gln Asn Gln
1               5                   10                  15

Gln Glu Lys
```

```
<210> SEQ ID NO 12
<211> LENGTH: 28
<212> TYPE: PRT
<213> ORGANISM: Human immunodeficiency virus

<400> SEQUENCE: 12

Asp Lys Glu Ile Ser Asn Tyr Thr Lys Thr Ile Tyr Lys Leu Leu Glu
1               5                   10                  15

Lys Ser Gln Asn Gln Gln Glu Glu Asn Glu Lys Asp
            20                  25

<210> SEQ ID NO 13
<211> LENGTH: 28
<212> TYPE: PRT
<213> ORGANISM: Human immunodeficiency virus

<400> SEQUENCE: 13

Asp Lys Glu Ile Ser Asn Tyr Thr Asp Thr Ile Tyr Lys Leu Leu Thr
1               5                   10                  15

Glu Ser Gln Ser Gln Gln Asp Lys Asn Glu Lys Asp
            20                  25

<210> SEQ ID NO 14
<211> LENGTH: 28
<212> TYPE: PRT
<213> ORGANISM: Artificial sequence
<220> FEATURE:
<223> OTHER INFORMATION: Synthetic peptide

<400> SEQUENCE: 14

Asp Lys Glu Ile Ser Asn Tyr Thr Lys Thr Ile Tyr Lys Leu Leu Glu
1               5                   10                  15

Lys Ser Gln Asn Gln Gln Asp Lys Asn Glu Lys Asp
            20                  25

<210> SEQ ID NO 15
<211> LENGTH: 28
<212> TYPE: PRT
<213> ORGANISM: Artificial sequence
<220> FEATURE:
<223> OTHER INFORMATION: Synthetic peptide

<400> SEQUENCE: 15

Asp Arg Glu Ile Ser Asn Tyr Thr Asp Thr Ile Tyr Arg Leu Leu Glu
1               5                   10                  15

Asp Ser Gln Asn Gln Gln Glu Lys Asn Glu Lys Asp
            20                  25

<210> SEQ ID NO 16
<211> LENGTH: 28
<212> TYPE: PRT
<213> ORGANISM: Artificial sequence
<220> FEATURE:
<223> OTHER INFORMATION: Synthetic peptide

<400> SEQUENCE: 16

Glu Arg Glu Ile Asp Asn Tyr Thr Gly Leu Ile Tyr Thr Leu Ile Glu
1               5                   10                  15

Glu Ser Gln Asn Gln Gln Glu Lys Asn Glu Gln Glu
            20                  25

<210> SEQ ID NO 17
<211> LENGTH: 50
```

```
<212> TYPE: PRT
<213> ORGANISM: Human immunodeficiency virus

<400> SEQUENCE: 17

Asn Tyr Thr Lys Thr Ile Tyr Lys Leu Leu Glu Lys Ser Gln Asn Gln
1               5                   10                  15

Gln Glu Glu Asn Glu Lys Asp Leu Leu Ala Leu Asp Ser Trp Asn Asn
                20                  25                  30

Leu Trp Asn Trp Phe Asp Ile Ser Asn Trp Leu Trp Tyr Ile Lys Ile
        35                  40                  45

Phe Ile
    50

<210> SEQ ID NO 18
<211> LENGTH: 26
<212> TYPE: PRT
<213> ORGANISM: Human immunodeficiency virus

<400> SEQUENCE: 18

Glu Val Ser Asn Tyr Thr Lys Thr Ile Tyr Lys Leu Leu Glu Lys Ser
1               5                   10                  15

Gln Asn Gln Gln Glu Glu Asn Glu Lys Asp
                20                  25

<210> SEQ ID NO 19
<211> LENGTH: 26
<212> TYPE: PRT
<213> ORGANISM: Human immunodeficiency virus

<400> SEQUENCE: 19

Glu Ile Ser Asn Tyr Thr Asn Thr Ile Tyr Arg Leu Leu Glu Asp Ser
1               5                   10                  15

Gln Asn Gln Gln Glu Lys Asn Glu Lys Asp
                20                  25

<210> SEQ ID NO 20
<211> LENGTH: 26
<212> TYPE: PRT
<213> ORGANISM: Human immunodeficiency virus

<400> SEQUENCE: 20

Glu Val Ser Asn Tyr Thr Asn Thr Ile Tyr Arg Leu Leu Glu Asp Ser
1               5                   10                  15

Gln Ser Gln Gln Glu Lys Asn Glu Lys Asp
                20                  25

<210> SEQ ID NO 21
<211> LENGTH: 26
<212> TYPE: PRT
<213> ORGANISM: Human immunodeficiency virus

<400> SEQUENCE: 21

Glu Ile Ser Asn Tyr Thr Asn Ile Ile Phe Gly Leu Leu Glu Asp Ser
1               5                   10                  15

Gln Asn Gln Gln Glu Arg Asn Glu Lys Asp
                20                  25

<210> SEQ ID NO 22
<211> LENGTH: 26
<212> TYPE: PRT
<213> ORGANISM: Human immunodeficiency virus

<400> SEQUENCE: 22
```

Glu Ile Ser Asn Tyr Thr Asp Thr Ile Tyr Lys Leu Leu Thr Glu Ser
1               5                   10                  15

Gln Thr Gln Gln Asp Lys Asn Glu Lys Asp
            20                  25

<210> SEQ ID NO 23
<211> LENGTH: 26
<212> TYPE: PRT
<213> ORGANISM: Human immunodeficiency virus

<400> SEQUENCE: 23

Glu Val Ser Asn Tyr Thr Phe Thr Ile Tyr Gln Leu Leu Glu Glu Ser
1               5                   10                  15

Gln Tyr Gln Gln Glu Gln Asn Glu Lys Asp
            20                  25

<210> SEQ ID NO 24
<211> LENGTH: 26
<212> TYPE: PRT
<213> ORGANISM: Human immunodeficiency virus

<400> SEQUENCE: 24

Glu Ile Ser Asn Tyr Thr Asp Thr Ile Tyr Arg Leu Leu Glu Asp Ser
1               5                   10                  15

Gln Asn Gln Gln Glu Lys Asn Glu Lys Asp
            20                  25

<210> SEQ ID NO 25
<211> LENGTH: 26
<212> TYPE: PRT
<213> ORGANISM: Human immunodeficiency virus

<400> SEQUENCE: 25

Glu Ile Asp Asn Tyr Thr Gly Leu Ile Tyr Thr Leu Ile Glu Glu Ser
1               5                   10                  15

Gln Asn Gln Gln Glu Lys Asn Glu Gln Glu
            20                  25

<210> SEQ ID NO 26
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: "Xaa" denotes Ser, Asn, Gly, Asp or Glu
<220> FEATURE:
<221> NAME/KEY: MISC_FEATURE
<222> LOCATION: (5)..(5)
<223> OTHER INFORMATION: "Xaa" denotes Thr, Ile or Leu
<220> FEATURE:
<221> NAME/KEY: MISC_FEATURE
<222> LOCATION: (8)..(8)
<223> OTHER INFORMATION: "Xaa" denotes Thr, Asn, Arg, Ser, Thr or Lys
<220> FEATURE:
<221> NAME/KEY: MISC_FEATURE
<222> LOCATION: (10)..(10)
<223> OTHER INFORMATION: "Xaa" denotes Leu or Ile
<220> FEATURE:
<221> NAME/KEY: MISC_FEATURE
<222> LOCATION: (12)..(12)
<223> OTHER INFORMATION: "Xaa" denotes Asp, Glu, Val, Lys or Gln
<220> FEATURE:
<221> NAME/KEY: MISC_FEATURE
<222> LOCATION: (19)..(19)
<223> OTHER INFORMATION: "Xaa" denotes Lys, Gln, Asn, Arg or Glu

```
<220> FEATURE:
<221> NAME/KEY: MISC_FEATURE
<222> LOCATION: (22)..(22)
<223> OTHER INFORMATION: "Xaa" denotes Gln, Arg or Lys

<400> SEQUENCE: 26

Asn Tyr Thr Xaa Xaa Ile Tyr Xaa Leu Xaa Glu Xaa Ser Gln Asn Gln
1               5                   10                  15

Gln Glu Xaa Asn Glu Xaa
            20

<210> SEQ ID NO 27
<211> LENGTH: 22
<212> TYPE: PRT
<213> ORGANISM: Artificial sequence
<220> FEATURE:
<223> OTHER INFORMATION: Synthetic peptide

<400> SEQUENCE: 27

Asn Tyr Thr Asp Thr Ile Tyr Lys Leu Leu Glu Lys Ser Gln Asn Gln
1               5                   10                  15

Gln Glu Glu Asn Glu Lys
            20

<210> SEQ ID NO 28
<211> LENGTH: 22
<212> TYPE: PRT
<213> ORGANISM: Artificial sequence
<220> FEATURE:
<223> OTHER INFORMATION: Synthetic peptide

<400> SEQUENCE: 28

Asn Tyr Thr Asn Thr Ile Tyr Arg Leu Leu Glu Asp Ser Gln Asn Gln
1               5                   10                  15

Gln Glu Lys Asn Glu Lys
            20

<210> SEQ ID NO 29
<211> LENGTH: 22
<212> TYPE: PRT
<213> ORGANISM: Artificial sequence
<220> FEATURE:
<223> OTHER INFORMATION: Synthetic peptide

<400> SEQUENCE: 29

Asn Tyr Thr Asn Leu Ile Tyr Thr Leu Ile Glu Glu Ser Gln Asn Gln
1               5                   10                  15

Gln Glu Lys Asn Glu Gln
            20

<210> SEQ ID NO 30
<211> LENGTH: 7
<212> TYPE: PRT
<213> ORGANISM: Artificial sequence
<220> FEATURE:
<223> OTHER INFORMATION: Synthetic peptide

<400> SEQUENCE: 30

Glu Asn Leu Tyr Phe Gln Ser
1               5

<210> SEQ ID NO 31
<211> LENGTH: 7
<212> TYPE: PRT
<213> ORGANISM: Artificial sequence
<220> FEATURE:
```

<223> OTHER INFORMATION: Synthetic peptide

<400> SEQUENCE: 31

Glu Asn Leu Tyr Phe Gln Gly
1               5

<210> SEQ ID NO 32
<211> LENGTH: 22
<212> TYPE: PRT
<213> ORGANISM: Human immunodeficiency virus

<400> SEQUENCE: 32

Asp Arg Glu Ile Ser Asn Tyr Thr Asp Thr Ile Tyr Arg Leu Leu Glu
1               5                   10                  15

Asp Ser Gln Asn Gln Gln
            20

<210> SEQ ID NO 33
<211> LENGTH: 22
<212> TYPE: PRT
<213> ORGANISM: Human immunodeficiency virus

<400> SEQUENCE: 33

Asp Arg Glu Ile Ser Asn Tyr Thr Glu Thr Ile Tyr Arg Leu Leu Glu
1               5                   10                  15

Asp Ser Gln Asn Gln Gln
            20

<210> SEQ ID NO 34
<211> LENGTH: 22
<212> TYPE: PRT
<213> ORGANISM: Human immunodeficiency virus

<400> SEQUENCE: 34

Asp Arg Glu Ile Ser Asn Tyr Thr Gly Thr Ile Tyr Arg Leu Leu Glu
1               5                   10                  15

Asp Ser Gln Asn Gln Gln
            20

<210> SEQ ID NO 35
<211> LENGTH: 22
<212> TYPE: PRT
<213> ORGANISM: Human immunodeficiency virus

<400> SEQUENCE: 35

Asp Arg Glu Ile Ser Asn Tyr Thr Asn Thr Ile Tyr Arg Leu Leu Glu
1               5                   10                  15

Asp Ser Gln Asn Gln Gln
            20

<210> SEQ ID NO 36
<211> LENGTH: 22
<212> TYPE: PRT
<213> ORGANISM: Human immunodeficiency virus

<400> SEQUENCE: 36

Asp Arg Glu Ile Ser Asn Tyr Thr Asp Ile Ile Tyr Arg Leu Leu Glu
1               5                   10                  15

Asp Ser Gln Asn Gln Gln
            20

<210> SEQ ID NO 37
<211> LENGTH: 22

```
<212> TYPE: PRT
<213> ORGANISM: Human immunodeficiency virus

<400> SEQUENCE: 37

Asp Arg Glu Ile Ser Asn Tyr Thr Asp Thr Ile Tyr Ser Leu Leu Glu
1               5                   10                  15

Asp Ser Gln Asn Gln Gln
            20

<210> SEQ ID NO 38
<211> LENGTH: 22
<212> TYPE: PRT
<213> ORGANISM: Human immunodeficiency virus

<400> SEQUENCE: 38

Asp Arg Glu Ile Ser Asn Tyr Thr Asp Thr Ile Tyr Arg Leu Leu Glu
1               5                   10                  15

Glu Ser Gln Asn Gln Gln
            20

<210> SEQ ID NO 39
<211> LENGTH: 22
<212> TYPE: PRT
<213> ORGANISM: Human immunodeficiency virus

<400> SEQUENCE: 39

Asp Arg Glu Ile Ser Asn Tyr Thr Asp Thr Ile Tyr Arg Leu Leu Glu
1               5                   10                  15

Val Ser Gln Asn Gln Gln
            20

<210> SEQ ID NO 40
<211> LENGTH: 22
<212> TYPE: PRT
<213> ORGANISM: Human immunodeficiency virus

<400> SEQUENCE: 40

Asp Arg Glu Ile Ser Asn Tyr Thr Asp Thr Ile Tyr Arg Leu Leu Glu
1               5                   10                  15

Asp Ser Gln Ile Gln Gln
            20

<210> SEQ ID NO 41
<211> LENGTH: 22
<212> TYPE: PRT
<213> ORGANISM: Human immunodeficiency virus

<400> SEQUENCE: 41

Asp Arg Glu Ile Ser Asn Tyr Thr Asp Thr Ile Tyr Arg Leu Leu Glu
1               5                   10                  15

Asp Ser Gln Ser Gln Gln
            20

<210> SEQ ID NO 42
<211> LENGTH: 22
<212> TYPE: PRT
<213> ORGANISM: Human immunodeficiency virus

<400> SEQUENCE: 42

Asp Arg Glu Ile Ser Asn Tyr Thr Asp Thr Ile Tyr Arg Leu Leu Glu
1               5                   10                  15

Asp Ser Gln Thr Gln Gln
            20
```

```
<210> SEQ ID NO 43
<211> LENGTH: 22
<212> TYPE: PRT
<213> ORGANISM: Human immunodeficiency virus

<400> SEQUENCE: 43

Asp Arg Glu Ile Ser Asn Tyr Ser Asp Thr Ile Tyr Arg Leu Leu Glu
1               5                   10                  15

Ala Ser Gln Asn Gln Gln
            20

<210> SEQ ID NO 44
<211> LENGTH: 22
<212> TYPE: PRT
<213> ORGANISM: Human immunodeficiency virus

<400> SEQUENCE: 44

Asp Arg Glu Ile Asn Asn Tyr Thr Asp Ile Ile Tyr Arg Leu Leu Glu
1               5                   10                  15

Asp Ser Gln Asn Gln Gln
            20

<210> SEQ ID NO 45
<211> LENGTH: 22
<212> TYPE: PRT
<213> ORGANISM: Human immunodeficiency virus

<400> SEQUENCE: 45

Asp Lys Glu Ile Asn Asn Tyr Thr Asp Thr Ile Tyr Arg Leu Leu Glu
1               5                   10                  15

Asp Ser Gln Asn Gln Gln
            20

<210> SEQ ID NO 46
<211> LENGTH: 22
<212> TYPE: PRT
<213> ORGANISM: Human immunodeficiency virus

<400> SEQUENCE: 46

Asp Arg Glu Ile Asn Asn Tyr Thr Asn Thr Ile Tyr Arg Leu Leu Glu
1               5                   10                  15

Asp Ser Gln Asn Gln Gln
            20

<210> SEQ ID NO 47
<211> LENGTH: 22
<212> TYPE: PRT
<213> ORGANISM: Human immunodeficiency virus

<400> SEQUENCE: 47

Asp Arg Glu Ile Asn Asn Tyr Thr Gln Thr Ile Tyr Arg Leu Leu Glu
1               5                   10                  15

Asp Ser Gln Asn Gln Gln
            20

<210> SEQ ID NO 48
<211> LENGTH: 22
<212> TYPE: PRT
<213> ORGANISM: Human immunodeficiency virus

<400> SEQUENCE: 48

Asp Arg Glu Ile Ser Asn Tyr Thr Asp Thr Ile Tyr Lys Leu Leu Glu
```

```
                           1               5              10              15

Asp Ser Gln Ile Gln Gln
            20

<210> SEQ ID NO 49
<211> LENGTH: 22
<212> TYPE: PRT
<213> ORGANISM: Human immunodeficiency virus

<400> SEQUENCE: 49

Asp Arg Glu Ile Ser Asn Tyr Thr Glu Thr Ile Tyr Lys Leu Leu Glu
1               5                   10                  15

Asp Ser Gln Asn Gln Gln
            20

<210> SEQ ID NO 50
<211> LENGTH: 22
<212> TYPE: PRT
<213> ORGANISM: Human immunodeficiency virus

<400> SEQUENCE: 50

Asp Arg Glu Ile Ser Asn Tyr Thr Asn Thr Ile Tyr Arg Leu Leu Glu
1               5                   10                  15

Asp Ser Gln Ile Gln Gln
            20

<210> SEQ ID NO 51
<211> LENGTH: 19
<212> TYPE: PRT
<213> ORGANISM: Human immunodeficiency virus

<400> SEQUENCE: 51

Asn Tyr Thr Asp Thr Ile Tyr Lys Leu Leu Thr Glu Ser Gln Ser Gln
1               5                   10                  15

Gln Asp Lys

<210> SEQ ID NO 52
<211> LENGTH: 19
<212> TYPE: PRT
<213> ORGANISM: Human immunodeficiency virus

<400> SEQUENCE: 52

Asn Tyr Thr Lys Thr Ile Tyr Lys Leu Leu Glu Lys Ser Gln Asn Gln
1               5                   10                  15

Gln Asp Lys
```

HIV-1 GP41 NEUTRALIZATION DOMAIN AND USE THEREOF

This application is a U.S. National Stage Application of PCT Patent Application No. PCT/US2008/072764 filed Aug. 11, 2008 and claims benefit of priority to U.S. Provisional Patent Application Ser. No. 60/954,862 filed Aug. 9, 2007, the contents of each of which is are incorporated herein by reference in their entirety.

This invention was made with support from the National Institutes of Health (Grant No. AI46383). The U.S. government may have certain rights in this present invention.

BACKGROUND OF THE INVENTION

The heptad repeat region 2 (HR2) of HIV-1 gp41 protein is involved in the formation of a coiled-coil structure with an N-terminal heptad repeat region on gp41 (HR1) that plays an important role in fusion. Binding of gp120 to the CD4 receptor results in a conformational rearrangement that is believed to expose portions of gp41 and initiate its rearrangement into a six helix bundle. An important role for this rearrangement in infection is indicated by the potent inhibition of infection by a large helical peptide derived from the HR2 domain that binds to a portion of HR1 and prevents the six helix bundle formation. This peptide, marketed as the antiviral drug FUZEON®, is composed of amino acid residues $CH_3CO$-Tyr-Thr-Ser-Leu-Ile-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Ala-Ser-Leu-Trp-Asn-Trp-Phe-$NH_2$ (SEQ ID NO:1).

Neutralization is the ability of antibody to bind to and inactivate virus infectivity. Neutralization by antibody can be mediated by a number of different mechanisms including aggregation of virions, destabilization of the virion structure, inhibition of virion attachment to target cells, inhibition of the fusion of the virion lipid membrane with the membrane of the host cell, inhibition of the entry of the genome of non-enveloped viruses into the cell cytoplasm, blocking of protein rearrangements needed for one of these functions, inhibition of a function of the virion core through a signal transduced by an antibody, and binding to nascent virions to block their budding or release from the cell surface. A virus may be neutralized by several different mechanisms because several unique epitopes may be sited in different locations on the virion and paratope and other properties of the reacting antibody may vary.

A variety of epitopes for HIV-1 binding antibodies are known in the art. Such epitopes are found in gp120, and gp41. See, for example, *HIV Molecular Immunology* (2002) Korber et al. ed., Los Alamos National Laboratory, Theoretical Biology and Biophysics, Los Alamos, N. Mex. LA-DR 03-5816. Although many antibody binding sites have been described in gp41, only a few lead to neutralization. For example, three monoclonal antibodies isolated from infected humans, 2F5, 4E10 and Z13, have been shown to recognize sequences in the membrane proximal external region (MPER) of gp41. The epitopes recognized by these monoclonal antibodies possess the attractive features that they are highly conserved and mediate relatively potent neutralization of virions, including viruses that are resistant to standard antibodies that target the major sites on gp120. The predominant disadvantage of these epitopes is that they are poorly immunogenic.

Recent evidence suggests a key property of the MPER-specific monoclonal antibodies is recognition of lipid components of the adjacent membrane in addition to binding to a peptide determinant on gp41 (Alam, et al. (2007) *J. Immunol.* 178:4424-4435). As a result, these antibodies also bind to normal cellular lipid components, including cardiolipin, and thus possess some autoimmune properties. It has been suggested that this autoreactive property accounts for the inability of most individuals to produce similar antibodies with HIV-neutralizing properties.

A series of nineteen monoclonal antibodies and Fab fragments have been described that have been mapped to gp41 "Cluster II", defined by reactivity with a fusion protein that contains the sequence Ser-Leu-Ile-Glu-Glu-Ser-Gln-Asn-Gln-Gln-Glu-Lys-Asn-Glu-Gln-Glu-Leu-Leu-Glu-Leu (SEQ ID NO:2), corresponding to gp41 residues 644-663 (HIV Immunology and HIV/SIV Vaccine Database 2003). However, all of the monoclonal antibodies mapped to this region have been described as "non-neutralizing" (Gorny and Zolla-Pazner (2003) In *HIV Immunology and HIV/SIV Vaccine Databases*. Korber, et al., editors. Publisher: Los Alamos National Laboratory, Theoretical Biology and Biophysics, Los Alamos, N. Mex. LA-UR 04-8162. pp. 37-51). In addition, six gp41-specific Fabs have been assigned to "Cluster III", defined as a conformational epitope involving amino acid residues 619-648, and these too were characterized as non-neutralizing. The lack of neutralizing activity of the previously described monoclonal antibodies and Fabs suggests that these reagents would not be useful in the neutralization of HIV and that therefore this region would not be a useful vaccine target.

Similarly, WO 2005/111621 suggests epitopes of gp41 including the disulfide-loop region of gp41 that links the N-HR and C-HR regions (amino acid residues 581 to 628), the N-HR region of gp41 (amino acid residues 546 to 581), the C-HR of gp41 (amino acid residues 628 to 661), and the membrane proximal region of gp41 (amino acid residues 657 to amino acids 684). However, neutralizing antibodies to each region are not provided.

SUMMARY OF THE INVENTION

The present invention is an isolated peptide containing the amino acid sequence set forth in SEQ ID NO:26. In some embodiments, the peptide is recognized by an antibody which neutralizes at least one HIV-1 primary isolate, wherein the HIV-1 primary isolate is from clade A, clade B, clade C, clade D, or clade E. In other embodiments the peptide is fused to a heterologous carrier protein. In yet other embodiments a peptide having 50% sequence identity with the peptide of SEQ ID NO:26 is provided. A vaccine containing the peptide of invention alone or in combination with a pharmaceutically acceptable carrier or vehicle is also provided, as is an isolated nucleic acid molecule encoding the peptide, an expression vector containing said nucleic acid molecule, and a host cell harboring said vector.

The present invention is also an isolated monoclonal antibody which recognizes a peptide containing the amino acid sequence set forth in SEQ ID NO:26. In certain embodiments, the antibody neutralizes at least one HIV-1 primary isolate, wherein said HIV-1 primary isolate is from clade A, clade B, clade C, clade D, or clade E.

The present invention also embraces a method for stimulating the formation of antibodies that neutralize infection by an HIV isolate by administering to a subject a composition containing a peptide of the invention or a vaccine containing the same.

BRIEF DESCRIPTION OF THE DRAWINGS

FIG. 1 shows the localization of 53M autologous neutralization targets by comparing neutralizing activities of 53M serum for recombinant Envs in which various domains of 53M (open) were switched with the corresponding regions of 133M Env (shaded).

FIG. 2 shows homologies in gp41 ectodomain for p1531 (SEQ ID NO:3) and six subtype C sequences (C1, 133 MPB3.8E, SEQ ID NO:4; C2, 106FPB9Env, SEQ ID NO:5; C3, 53 MPB21Env, SEQ ID NO:6; C4, 55FPB4aEnv, SEQ ID NO:7; C5, 135 MPL23aE, SEQ ID NO:8; and C6, 109FPB60En, SEQ ID NO:9). The boxed area (residues 637-655) indicates a polymorphic region in the HR2 domain containing several charged residues unique to 53M. 2F5 and 4E10 epitopes are indicated by underlining.

FIG. 8 shows the sequence homology of the MDER and surrounding region for six primary subtype C primary Envs (53 MP, SEQ ID NO:18; 133M, SEQ ID NO:19; 106F, SEQ ID NO:20; 55F, SEQ ID NO:21; 135 MPL23A, SEQ ID NO:22; and 109F, SEQ ID NO:23), and compares these sequences to the subtype B and C consensus sequences (SEQ ID NO:24 and SEQ ID NO:25, respectively). Positions highly specific for the 53M sequence are indicated with an asterisk.

DETAILED DESCRIPTION OF THE INVENTION

Figure 3:
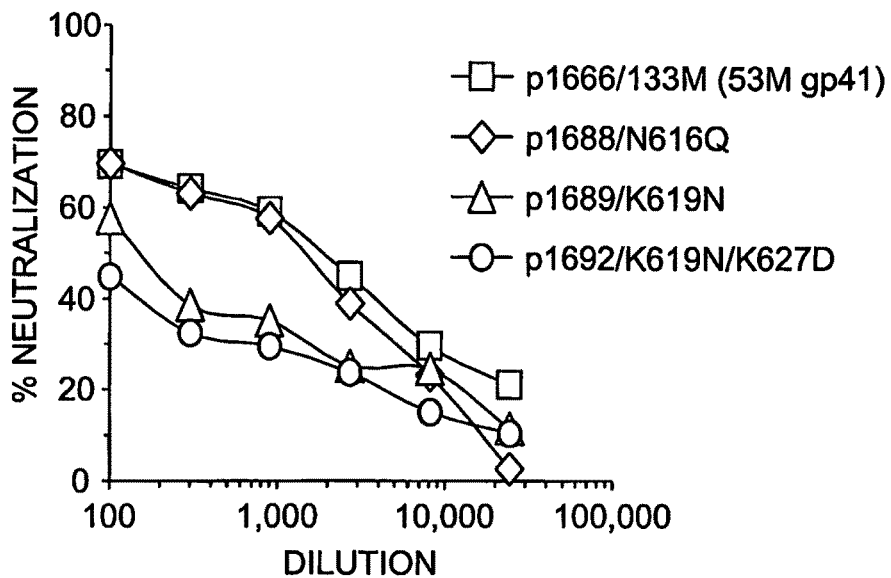
FIG. 3 shows the effect of replacing specific residues in the MDER of a chimeric Env (p1666, SEQ ID NO:10) with the MDER of 53M on sensitivity to neutralization by 53M serum. Analysis was carried out with mutants in the 637-648 region of HR2. The numbering depicted is based by convention on the HXB2 sequence (SEQ ID NO:11); these residues are at positions 616-627 in the 53M sequence.

The present invention is a region in HIV-1 gp41 that contains, either in part or in whole, an epitope that allows potent neutralization of resistant virus particles. This site is present in the C-terminal heptad repeat region of gp41 (HR2), and adjacent to, but distinct from the MPER. This region is referred to herein as the Membrane Distal External Region (MDER). The MDER sequence finds application in the development of prophylactic vaccines that direct the formation of antibodies to sites dependent on sequences in the MDER that have broad neutralizing activities against otherwise-resistant HIV-1 isolates, which conventional vaccines have not been able to induce. Moreover, because different isolates may have variant forms of MDER epitopes, neutralization breadth can require the use of a multivalent immunogen that contains multiple forms of the MDER sequences. Vaccines of the invention can be used to reduce the likelihood of contracting HIV-infections, and reduce the rate of spread of the virus in a given population.

Accordingly, the present invention relates to an isolated MDER peptide. The peptide of the invention is isolated in the sense that it is substantially removed from any other contaminating molecules (e.g., carbohydrates, proteins, DNA, etc.). As used herein, a peptide is a chain of 4 to 22 amino acid residues, which may or may not be post-translationally modified (e.g., glycosylation or phosphorylation). In particular embodiments, a peptide of the invention is 4, 5, 6, 7, 8, 9, 10, 11, 12, 13, 14, 15, 16, 17, 18, 19, 20, 21 or 22 amino acid residues in length. It is further contemplated that all or a portion of the MDER peptide may be a component of a conformational epitope. As such, some embodiments embrace the use of the instant MDER peptide in combination with additional sequences derived from other regions of gp41 or gp120, wherein said regions are either covalently or non-covalently complexed with the MDER peptide of the invention. The peptide of the invention is referred to as being isolated in that it is at least 60% by weight (dry weight) the peptide of interest. Desirably, the peptide is at least 75%, more desirably at least 90%, and most desirably at least 99%, by weight, the peptide of interest. Purity can be measured by any appropriate standard method, e.g., column chromatography, polyacrylamide gel electrophoresis, or HPLC analysis.

An MDER peptide of the invention includes amino acid residues located in the HR2 domain of HIV-1 gp41 that are flanked by Asn-Tyr-Thr on the N-terminus and Asn-Glu-Gln/Lys on the C-terminus. In one embodiment, an MDER peptide of the invention contains all or a portion of the amino acid sequence Asn-Tyr-Thr-$Xaa_1$-$Xaa_2$-Ile-Tyr-$Xaa_3$-Leu-$Xaa_4$-Glu-$Xaa_5$-Ser-Gln-Asn-Gln-Gln-Glu-$Xaa_6$-Asn-Glu-$Xaa_7$ (SEQ ID NO:26), wherein $Xaa_1$ is Ser, Asn, Gly, Asp or Glu; $Xaa_2$ is Thr, Ile or Leu; $Xaa_3$ is Thr, Asn, Arg, Ser, Thr or Lys; $Xaa_4$ is Leu or Ile; $Xaa_5$ is Asp, Glu, Val, Lys or Gln; $Xaa_6$ is Lys, Gln, Asn, Arg or Glu; and $Xaa_7$ is Gln, Arg or Lys. In particular embodiments, an MDER peptide of the invention contains all or a portion of the amino acid sequence Asn-Tyr-Thr-Asp-Thr-Ile-Tyr-Lys-Leu-Leu-Glu-Lys-Ser-Gln-Asn-Gln-Gln-Glu-Glu-Asn-Glu-Lys (SEQ ID NO:27), Asn-Tyr-Thr-Asn-Thr-Ile-Tyr-Arg-Leu-Leu-Glu-Asp-Ser-Gln-Asn-Gln-Gln-Glu-Lys-Asn-Glu-Lys (SEQ ID NO:28), or Asn-Tyr-Thr-Asn-Leu-Ile-Tyr-Thr-Leu-Ile-Glu-Glu-Ser-Gln-Asn-Gln-Gln-Glu-Lys-Asn-Glu-Gln (SEQ ID NO:29).

While specific amino acid substitutions of the MDER have been identified, the present invention also embraces peptides that are partially identical, e.g., at least 50%, 60%, 70%, 80%, 90%, 95%, or 97%) to the amino acid sequence set forth in SEQ ID NO:26. For example, it is contemplated that one or more of the non-degenerate residues of SEQ ID NO:26 can be substituted with conserved amino acid residues which retain structural and functional characteristics of the MDER peptide of SEQ ID NO:26. For example, it is contemplated that one or more of the residues of SEQ ID NO:26 can be substituted so long as said substitutions retain the structural and functional characteristics of the MDER peptide of SEQ ID NO:26. As is conventional in the art, an amino acid substitution refers to the replacement of at least one existing amino acid residue in a predetermined sequence with another, conserved amino acid residue. The results peptide can differ from the parent MDER peptide by as many as 1, 2, 3, 4, 5, or 6 amino acid residue substitutions. By way of illustration, the aromatic amino acid residue Tyr at position 2 and/or 7 of SEQ ID NO:26 can be replaced with another aromatic amino acid residue such as Phe, Trp or His. Similarly, aliphatic amino acid residues Ile or Leu at positions 6 or 8, respectively, of SEQ ID NO:26 can be replaced with another aliphatic amino acid residue such as Ile, Val or Leu. Other such substitutions between hydrophobic, charged, or polar amino acid residues can be made as is conventionally practiced in the art of protein chemistry. Specific guidance for exemplary substitutions is disclosed herein in the Figures and Table 1.

An MDER peptide and portions thereof can be recombinantly produced (e.g., in vitro or in vivo), purified from a natural source, or chemically synthesized. For yield and ease in purification, it is conventional in the art to produce peptides and peptide fragments by recombinant protein methodologies. Accordingly, particular embodiments of the present invention embrace nucleic acid molecules encoding MDER peptides and vectors and host cells containing nucleic acid molecules encoding MDER peptides for use in MDER peptide and vaccine production. Nucleic acid molecules within the invention can be cDNA, genomic DNA, synthetic DNA, or RNA, and can be double-stranded or single-stranded (i.e., either a sense or an antisense strand). Nucleic acid molecule so the invention can be produced, for example, by the polymerase chain reaction (PCR) or generated by treatment of longer nucleic acid molecules with one or more restriction endonucleases thereby releasing the nucleic acid molecule of interest. A ribonucleic acid (RNA) molecule can be produced by in vitro transcription.

The nucleic acid molecules of the invention can be naturally occurring sequences (e.g., sequences cloned from HIV-1 itself) or sequences that differ from those that occur naturally, but, due to the degeneracy of the genetic code, encode the same MDER peptide. In addition, these nucleic acid molecules are not limited to sequences that only encode an MDER peptide, and thus, can include coding sequence that encodes a heterologous carrier protein, as well as non-coding sequences, e.g., regulatory sequences.

The nucleic acid molecules of the invention can be synthesized (for example, by phosphoramidite-based synthesis) or obtained from a natural source (e.g., a virus or a recombinant virus).

The isolated nucleic acid molecules of the invention encompass fragments that are not found as such in the natural state. Thus, the invention encompasses recombinant molecules, such as those in which a nucleic acid molecule is incorporated into a vector (for example, a plasmid or viral vector) or is joined to a second nucleic acid sequence such that the joined sequences encode a fusion protein.

An isolated nucleic acid molecule encoding an MDER peptide can be incorporated into a vector, e.g., for the purposes of cloning or other laboratory manipulations, recombinant peptide production, or gene delivery. In particular embodiments, the vector is an expression vector, which can include a regulatory element such as the cytomegalovirus hCMV immediate early gene, the early promoter of SV40 adenovirus, the late promoter of SV40 adenovirus, the lac system, the TAC system, the TRC system, the major operator and promoter regions of phage, the control regions of fd coat protein, the promoter for 3-phosphoglycerate kinase, the promoters of acid phosphatase, or the promoters of the yeast mating factors.

Exemplary vectors include bacterial artificial chromosomes, cosmids, yeast artificial chromosomes, phage, plasmids, lipid vectors and viral vectors (e.g., a retrovirus). Particularly preferred are expression vectors which express the peptide of the invention as part of a fusion protein. Suitable fusion protein expression vectors are described in U.S. Pat. No. 5,643,756. By the term express, expresses or expression of a nucleic acid molecule it is meant that the sequence is transcribed, and optionally, translated. Typically, transcription and translation of a coding sequence will result in production of an MDER peptide.

Methods for producing recombinant proteins in vivo (i.e., cell-based) are routinely practiced in the art by introducing the nucleic acid molecule of interest into a recombinant expression vector in a form suitable for expression of the peptide in a host cell. A suitable form for expression provides that the recombinant expression vector includes one or more regulatory elements operatively-linked to the nucleic acid molecule encoding the peptide of interest in a manner which allows for transcription of the nucleic acids into mRNA and translation of the mRNA into the peptide. Regulatory elements can include promoters, enhancers and other expression control elements (e.g., polyadenylation signals). Such regulatory elements and vectors encoding the same are known to those skilled in the art and are described in Goeddel, Gene Expression Technology: Methods in Enzymology 185, Academic Press, San Diego, Calif. (1990). Suitable vectors for recombinant protein expression in mammalian, yeast, plant or prokaryotic systems are commercially available from such sources as STRATAGENE, INVITROGEN, Pharmacia and the like.

Introduction of the recombinant expression vector into a host cell (e.g., of eukaryotic or prokaryotic origin) can be carried out using any conventional technique for transforming cells. Suitable methods for transforming host cells are found in Sambrook, et al. (Molecular Cloning: A Laboratory Manual, 3rd Edition, Cold Spring Harbor Laboratory Press (2000)) and other laboratory manuals. The number of host cells transformed with a nucleic acid molecule encoding an MDER peptide will depend, at least in part, upon the type of recombinant expression vector used and the type of transformation technique used. A recombinant peptide can be expressed transiently, or more typically, stably expressed by integrating the recombinant expression vector into the genome of the host cell or by episomal maintenance of the vector.

Once produced, an MDER peptide can be recovered from the culture medium as a secreted peptide, or alternatively recovered from host cell lysates when directly expressed without a secretory signal. As such, it may be necessary to purify the MDER peptide from recombinant cell proteins or polypeptides using conventional protein purification methods to obtain preparations that are substantially homogeneous to the MDER peptide. As a first step, the culture medium or lysate is centrifuged to remove particulate cell debris. The membrane and soluble protein fractions are then separated. The recombinant peptide may then be purified from the soluble protein fraction. The recombinant peptide thereafter is purified from contaminant soluble proteins and polypeptides using any of the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75; and ligand affinity chromatography.

In addition to recombinant production, an MDER peptide can be produced by direct peptide synthesis using solid-phase techniques (Merrifield (1963) J. Am. Chem. Soc. 85:2149-2154). Peptide synthesis can be performed using manual techniques or by automation. Automated synthesis can be achieved, for example, using APPLIED BIOSYSTEMS® 431A Peptide Synthesizer (Perkin Elmer, Boston, Mass.).

The MDER peptide of the invention can be produced by itself or as a component of a fusion or hybrid polypeptide or protein. For example a hybrid polypeptide can contain all or a portion of the MDER peptide of SEQ ID NO:26 fused to a heterologous carrier protein, i.e., a signal sequence for secretion and/or other polypeptide which will aid in the purification or immunogenicity of the MDER peptide. In one embodiment, the heterologous carrier protein has a specific cleavage site to remove the heterologous carrier protein from the MDER peptide. By way of further illustration, all or a portion of the MDER peptide of SEQ ID NO:26 can be fused to additional sequences of gp41 or gp120 (e.g., the HR1 region) to form a conformational epitope which neutralizes infection by HIV or enhances the immunogenicity of the MDER peptide.

In general, a signal sequence can be a component of the vector and should be one that is recognized and processed (i.e., cleaved by a signal peptidase) by the host cell. For production in a prokaryote, a prokaryotic signal sequence from, for example, alkaline phosphatase, penicillinase, lpp, or heat-stable enterotoxin II leaders can be used. For yeast secretion, one can use, e.g., the yeast invertase, alpha factor, or acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal can be used.

Other useful heterologous carrier protein which can be fused to an MDER peptide include those which increase expression or solubility of the fusion protein or aid in the purification of the fusion protein by acting as a ligand in affinity purification. Typical fusion expression vectors include pFUSE (Invivogen, San Diego, Calif.), pMAL (New England Biolabs, Beverly, Mass.) and pRIT5 (Pharmacia, Piscataway, N.J.) which fuse Fc, maltose E binding protein or protein A, respectively, to the target recombinant protein.

By way of illustration, all or a portion of an MDER peptide is fused to a protein comprising all or a portion of Friend MuLV gp70, preferably amino acids 1-33 or 1-263 of gp70 and, optionally, a His6 tag. The fusion protein can also include a specific cleavage site (Glu-Asn-Leu-Tyr-Phe-Gln-Ser (SEQ ID NO:30) or Glu-Asn-Leu-Tyr-Phe-Gln-Gly (SEQ ID NO:31)) for TEV protease (rTEV protease; GIBCO, Bethesda, Md.) immediately preceding the MDER peptide sequence. TEV protease cleaves its specific cleavage site between the Gln and Ser or Gly residues. The fusion protein can be purified on a Ni-NTA column if a His6 tag is present or by other suitable means. After digestion with TEV protease (50 U/ml at room temperature for 18 hours) the mixture is passed over a second Ni-NTA column to remove the gp70 carrier (and TEV protease, which also carries a His6 tag). Free MDER peptide is subsequently recovered in the flow-through fraction.

In accordance with various embodiments of the present invention, the MDER peptide is recognized by an antibody which neutralizes at least one HIV-1 primary isolate with a $ND_{90}$ of less than 100 µg/ml. In some embodiments, the MDER peptide is recognized by an antibody which neutralizes two or more HIV-1 primary isolates of the same clade (e.g., clade A, clade B, clade C, clade D, and clade E) with a $ND_{90}$ of less than 100 µg/ml. In other embodiments, the MDER peptide is recognized by an antibody which neutralizes two or more HIV-1 primary isolates of different clades (e.g., clade A, clade B, clade C, clade D, and clade E) with a $ND_{90}$ of less than 100 µg/ml. Further embodiments of the present invention embrace neutralization of one or more HIV-1 primary isolates with a $ND_{90}$ of less than 50 µg/ml; a $ND_{90}$ of less than 20 µg/ml; a $ND_{90}$ of less than 10 µg/ml; a $ND_{90}$ of less than 5 µg/ml; or a $ND_{90}$ of less than 1 µg/ml. Additional embodiments embrace neutralization of one or more HIV-1 primary isolates with a $ND_{50}$ of less than 50 µg/ml; a $ND_{50}$ of less than 20 µg/ml; a $ND_{50}$ of less than 10 µg/ml; a $ND_{50}$ of less than 5 µg/ml; or a $ND_{50}$ of less than 1 µg/ml.

In addition to use in immunoassays for anti-HIV antibodies and for the production of anti-HIV antiserum, the MDER peptides described herein are useful in vaccine compositions or compositions used to elicit a humoral immune response. Accordingly, MDER peptides of the invention find application as a prophylactic vaccine, to reduce the replication of HIV-1 in already-infected patients and limit the infectivity of virus in a vaccinated patient. Such therapeutic vaccines can be based on the dominant forms of the MDER sequence in a given patient, thereby increasing the efficacy of the vaccine. Such vaccines can include an MDER peptide, MDER peptide fragment, MDER fusion protein, or optionally an MDER nucleic acid molecule used alone or with a pharmaceutically acceptable vehicle or carrier. In various embodiments a pharmaceutically acceptable vehicle or carrier is an adjuvant; an aluminum salt or an oil-in-water emulsion; an emulsifying agent and a metabolizable oil; or an immunostimulating agent, and the composition is administered to the mammalian subject by injection.

In some embodiments, it may be desirable to administer combination vaccines having one component that elicits an immune response primarily against macrophage-tropic HIV strains and a second component that elicits an immune response primarily against T Cell-tropic HIV strains. It may also be desirable for either or both components to be composed of a mixture of antigens, e.g., a mixture of antigens each of which elicits an immune response to a particular HIV strain or group of HIV strains.

An additional use of this invention is in the form of therapeutic administration of pre-formed neutralizing antibodies, or antibody fragments, that target MDER peptides. Such antibody administrations find application in both prophylactic and therapeutic applications. Accordingly, a monoclonal antibody which specifically recognizes or binds to all or a portion of an MDER peptide is also embraced by the present invention. In one embodiment, such a monoclonal antibody neutralizes at least one HIV-1 primary isolate. In another embodiment, the monoclonal antibody neutralizes two or more HIV-1 primary isolates of the same clade (e.g., clade A, clade B, clade C, clade D, and clade E). In still another embodiment, the monoclonal antibody neutralizes two or more HIV-1 primary isolates of different clades (e.g., clade A, clade B, clade C, clade D, and clade E).

The members of a pair of molecules (for example, an antibody-epitope pair) are said to "specifically bind" to each other if they bind to each other with greater affinity than to other molecules. Thus, an antibody which specifically binds to a particular epitope within a MDER peptide binds to that particular MDER epitope with greater affinity than to other epitopes.

The term monoclonal antibody refers to an antibody obtained from a population of substantially homogeneous antibodies, i.e., the individual antibodies of the population are identical except for possible naturally occurring mutations that may be present in minor amounts. Monoclonal antibodies can be highly specific, being directed against a single epitope. Furthermore, in contrast to conventional (polyclonal) antibody preparations that typically include different antibodies directed against different epitopes (determinants), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies of the present invention can be made by the hybridoma method first described by Kohler, et al. ((1975) *Nature* 256:495), or can be made by recombinant DNA methods (see, e.g., U.S. Pat. No. 4,816,567). Monoclonal antibodies can also be isolated from phage antibody libraries using the techniques described in Clackson, et al. ((1991) *Nature* 352:624-628) and Marks, et al. (1991) *J. Mol. Biol.* 222:581 597), for example. In particular, monoclonal antibodies can be obtained by any technique that provides for the production of antibody molecules by continuous cell lines in culture such as described in Kohler et al ((1975) supra); the human B-cell hybridoma technique (Kosbor, et al. (1983) *Immunology Today* 4:72; Cole, et al. (1983) *Proc. Natl. Acad. Sci. USA* 80:2026), and the EBV-hybridoma technique (Cole, et al. (1983) *Monoclonal Antibodies and Cancer Therapy*, Alan R. Liss, Inc., pp. 77-96). The hybridoma producing the monoclonal antibody of this invention may be cultivated in vitro or in vivo. The ability to produce high titers of monoclonal antibodies in vivo makes this the presently preferred method of production.

Monoclonal antibodies of the invention can be of any immunoglobulin class including IgG, IgM, IgE, IgA, IgD and any subclass thereof. Monoclonal antibodies of human origin can be derived either by directly transforming human B cells, or by standard hybridoma techniques, using strains of mice that have been engineered to produce only human immunoglobulins (Fishwild, et al. (1996) *Nat. Biotech.* 14:845; Mendez, et al. (1997) *Nat. Genet.* 15:146; Abgenix, Inc., Freemont, Calif.; GenPharm, Inc., Palo Alto, Calif.).

Monoclonal antibodies of the invention also include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit, the desired binding specificity or biological activity (U.S. Pat. No. 4,816,567; and Morrison, et al. (1984) *Proc. Natl. Acad. Sci. USA* 81:6851-6855).

An antibody fragment, as defined for the purpose of the present invention, encompasses a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

Once produced, the specificity and ability of a monoclonal antibody to bind to an MDER peptide can be determined by western blot or immunoprecipitation analysis by standard methods, e.g., as described in Ausubel, et al. eds. (1993) *Current Protocols in Molecular Biology*, John Wiley & Sons, Inc. Moreover, the ability of a monoclonal antibody to neutralize one or more HIV-1 primary isolates can be determined by routine experimentation, e.g., as exemplified herein.

The invention also provides a method for stimulating the formation of antibodies capable of neutralizing infection by an HIV viral isolate in at least one mammalian species. Such a method includes immunizing a subject (i.e., a mammal) with a composition containing one or more MDER peptides so that antibodies capable of neutralizing infection by an HIV viral isolate are produced. Preferred peptides are those which can elicit antibodies which neutralize primary isolates in two or more clades (e.g., two or more of clades A, B, C, D, and E).

Antibody formation can be determined by obtaining a sample from the subject and evaluating whether the sample contains antibodies which specifically bind to the one or more MDER peptides (e.g., by ELISA assays) and are capable of neutralizing one or more HIV viral isolates (e.g., in a neutralization assay).

In accordance with the present invention, one or more MDER peptides can be combined with a suitable adjuvant (e.g., an aluminum salt) to create a vaccine. Vaccine formulations will contain an effective amount of the selected peptide antigen(s), i.e., an amount of peptide which, when combined with adjuvant, will cause the subject (e.g., chimpanzees, maques, baboons, or humans) vaccinated to produce a sufficient, specific immunological response to provide for formation of neutralizing antibodies for protection against subsequent exposure to HIV. The vaccine compositions can also be used therapeutically for treatment of subjects (e.g., chimpanzees, maques, baboons, or humans) already infected with HIV.

In many cases the vaccine will need to be administered more than once to bring about the desire therapeutic or prophylactic effect. The precise protocol (dosage and frequency of administration can be established through standard clinical trials. Those skilled in the art will be able to design suitable clinical-trials using the results of animal trials (e.g., studies conducted in non-human primates). Dosages may range from 0.1 mg/dose to 1 mg/dose, mg/dose, 100 mg/dose, or 250 mg/dose. The effective amount of a given peptide will depend on a number of factors including antigenicity and purity.

In general, the antigen and adjuvant are suspended in a small volume (generally 2 ml or less) of a pharmaceutically acceptable carrier. Adjuvants and vaccination protocols are discussed in U.S. Pat. No. 5,614,612.

The invention is described in greater detail by the following non-limiting examples.

Example 1

Neutralizing Activity of 53M Serum Samples

Studies were conducted on two sets of Envs and sera isolated from a cohort in Zambia (Li, et al. (2006) *J. Virol.* 80:5211-18). Sera samples 53M and 133M both possessed high autologous neutralizing titers, but while 133M serum did not neutralize any of the heterologous Envs, 53M serum also had a lower neutralizing activity for a number of additional primary Envs. To map the general location of the autologous neutralization targets in 53M Env, a series of recombinants was generated in which various domains were exchanged between 53M Env and 133M Env, a second primary clade C Env that was resistant to neutralization by 53M serum (FIG. 1). This approach utilized conveniently placed restriction sites present in the conserved regions following the V2 (BglII) and V5 (MfeI) domains, resulting in the generation of infectious recombinant Envs in which N-terminal gp120 domain (through C2, including V1/V2), C-terminal gp120 domains (V3-V5) and gp41 domains of the two Envs were exchanged. The sensitivities of the resulting chimeras to neutralization by 53M and 133M sera were compared to that of the wild-type Envs, as a way of evaluating the contribution of the various regions to neutralization by the autologous sera.

These studies indicate that for 53M Env, autologous targets were located in three separate regions. One target was located, at least in part, in the N-terminal domain that included the V1/V2 region. A major neutralization target (or targets) appeared to be contained in the central V3-V5 domain, as shown by the large reduction in neutralization by 53M serum upon replacement of this region, both by itself (p163 vs. p1663) and in combination with the N-terminal domain (p1661 vs. p1666). Replacing just the V3-V5 domains resulted in a decrease in neutralization titer from 1:16000 to 1:2900. A smaller, although still significant, effect was seen upon gp41 exchanges, with a neutralization titer of 1:1650 obtained for 53M serum against a chimeric Env containing the autologous gp41 domain in the 133M backbone (p1666).

These results demonstrate that multiple targets were responsible for the unusually high autologous neutralization sensitivity of 53M Env (~1:16000). This indicates that in general, high neutralization potency may require targeting multiple epitopes. Of interest is that 53M serum also possesses relative broad (although less potent) neutralizing activity for additional subtype C primary isolates (overall, 53M serum neutralized 9/12 subtype C isolates tested). Indeed, there is a high degree of homology of the MDER region amongst primary subtype C Env sequences (Table 2).

TABLE 2

| Primary Isolate | MDER Sequence | SEQ ID NO: | Number of Variations* |
|---|---|---|---|
| C.FI.94.FIN9401 | DREIS<u>NYT</u>DTIYRLLEDSQNQQ | 32 | 0 |
| C.ZA.97.ZA003 | DREIS<u>NYT</u>DTIYRLLEDSQNQQ | 32 | 0 |
| C.ZA.99.ZASW7 | DREIS<u>NYT</u>DTIYRLLEDSQNQQ | 32 | 0 |
| C.BW.00.00BW192113 | DREIS<u>NYT</u>ETIYRLLEDSQNQQ | 33 | 1 |
| C.BW.96.96BW06 | DREIS<u>NYT</u>GTIYRLLEDSQNQQ | 34 | 1 |
| C.UG.90.UG268A2 | DREIS<u>NYT</u>GTIYRLLEDSQNQQ | 34 | 1 |
| C.ZA.99.DU151 | DREIS<u>NYT</u>GTIYRLLEDSQNQQ | 34 | 1 |
| C.BI.91.BU91 | DREIS<u>NYT</u>NTIYRLLEDSQNQQ | 35 | 1 |
| C.BW.00.00BW17593 | DREIS<u>NYT</u>NTIYRLLEDSQNQQ | 35 | 1 |
| C.FI.91.FIN9158 | DREIS<u>NYT</u>NTIYRLLEDSQNQQ | 35 | 1 |
| C.IN.93.93IN904 | DREIS<u>NYT</u>NTIYRLLEDSQNQQ | 35 | 1 |
| C.IN.93.93IN905 | DREIS<u>NYT</u>NTIYRLLEDSQNQQ | 35 | 1 |
| C.ZA.98.98ZA445 | DREIS<u>NYT</u>NTIYRLLEDSQNQQ | 35 | 1 |
| C.IN.99.01IN565 | DREIS<u>NYT</u>DIIYRLLEDSQNQQ | 36 | 1 |
| B.BW.00.00BW17956 | DREIS<u>NYT</u>DTIYSLLEDSQNQQ | 37 | 1 |
| C.BW.96.96BWM01 | DREIS<u>NYT</u>DTIYRLLEESQNQQ | 38 | 1 |
| C.BW.96.96BW11801 | DREIS<u>NYT</u>DTIYRLLEVSQNQQ | 39 | 1 |
| C.BW.00.00BW18598 | DREIS<u>NYT</u>DTIYRLLEDSQIQQ | 40 | 1 |
| C.BW.00.00BW5031 | DREIS<u>NYT</u>DTIYRLLEDSQNQQ | 41 | 1 |
| C.ZA.97.97ZA012 | DREIS<u>NYT</u>DTIYRLLEDSQTQQ | 42 | 1 |
| C.ZA.98.TV019 | DREIS<u>NYS</u>DTIYRLLEASQNQQ | 43 | 2 |
| C.BW.00.00BW20636 | DREIN<u>NYT</u>DIIYRLLEDSQNQQ | 44 | 2 |
| C.MM.99.nIDU101 | DKEIN<u>NYT</u>DTIYRLLEDSQNQQ | 45 | 2 |
| C.IN.94.94IN11246 | DREIN<u>NYT</u>NTIYRLLEDSQNQQ | 46 | 2 |
| C.IN.93.93IN999 | DREIN<u>NYT</u>QTIYRLLEDSQNQQ | 47 | 2 |
| C.BW.98.98BWM01410 | DREIS<u>NYT</u>DTIYKLLEDSQIQQ | 48 | 2 |
| C.ZA.98.TV018 | DREIS<u>NYT</u>ETIYKLLEDSQNQQ | 49 | 2 |
| C.FI.92.FIN9210 | DREIS<u>NYT</u>NTIYRLLEDSQIQQ | 50 | 2 |

*Variations compared to consensus sequence:
DREIS<u>NYT</u>DTIYRLLEDSQNQQ; SEQ ID NO: 32

Example 2

Localization of gp41 Sequence that Mediates Autologous Neutralization

To identify the location of the epitope(s) responsible for the autologous neutralizing activity of 53M serum, the gp41 ectodomain sequences of six subtype isolates were analyzed to identify a sequence distinct from the other sequences. One particular region in the HR2 region was notably polymorphic, and the 53M sequence contained several charged resides that were unique for this sequence (indicated by the box in FIG. 2). This sequence was located approximately in the middle of the HR2 domain, and N-terminal to the MPER epitopes recognized by monoclonal antibodies 2F5 and 4E10.

To determine whether this region participated in the 53M gp41 neutralization epitope, several mutations were introduced at the polymorphic positions of this region in the chimeric Env that contained the gp41 region of 53M Env in the 133M Env background (p1666 in FIG. 1). The use of this chimeric Env allowed the isolation of the 53M gp41 targets from the other targets present in 53M gp120, and provided greater precision and specificity than if the parental Env was used. The Lys at position 640 (based on the HXB2 numbering system) that was unique in the 53M sequence was mutated to Asn (the residue at this position for 4 of the 6 subtype C Envs), and this was then combined with the mutation of the other unique Lys in the 53M sequence, Lys648, to Asp. In addition, to test whether the conserved Asn637 glycosylation site at the N-terminus of this region served as a masking element for the gp41 neutralization target, the glycan at this site was eliminated by converting Asn637 to Gln (plasmid 1688).

The removal of the flanking glycosylation site did not appreciably change the neutralizing activity of the autologous serum (FIG. 3), indicating that the putative glycan at this site was not a masking element. Mutating Lys640 to Asn, with or without a second mutation of Lys648 to Asp, resulted in a greater than 10-fold reduction in $IC_{50}$, from 1800 to 150 and <100, respectively. This indicated that the unique Lys640 residue was a central component of the gp41 autologous neutralization epitope, while the second unique Lys at position 648 may be a less critical component.

Example 3

Neutralization Sensitivity of Mutant 135M Env to 53M Serum

Figures 4, 5:
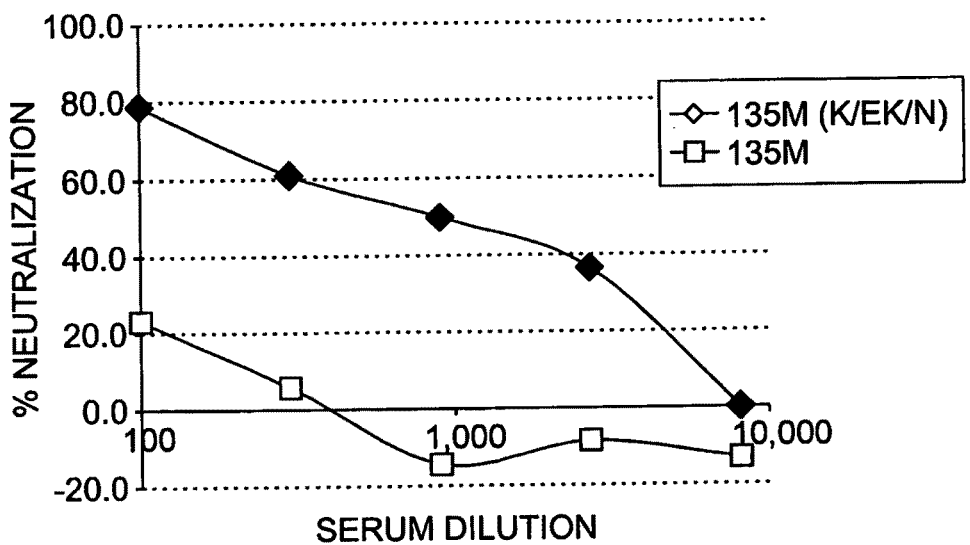
FIG. 4 shows the homology between the HR2 regions of 53M (53 MB21Env, SEQ ID NO:12) and 135M (135 MPL23aE, SEQ ID NO:13) gp41s. Differences are indicated with an asterisk. Also shown is the sequence of mutant 135M (K/EK/N) (SEQ ID NO:14), as well as the conserved sequences in Clade C (SEQ ID NO:15) and Clade B (SEQ ID NO:16).
FIG. 5 shows that the introduction of 53M residues into the MDER region of 135M Env results in sensitivity to neutralization by 53M serum.

To further confirm the role of the region in HR2 identified as a neutralization determinant, it was determined whether substituting sequences from this region into a resistant Env could introduce neutralization sensitivity to 53M serum. The HR2 sequence of the 135M Env was the most closely related to that of 53M, so 135M Env was selected as the recipient. Six positions in the 640-655 region of HR2 differed in sequence for 53M and 135M Envs; Lys vs. Asp at 640, Glu-Lys vs. Thr-Glu at 647/648, Asn vs. Ser at 651 and Glu-Glu vs. Asp-Lys at 654/655 (FIG. 4). The first four of these changes were introduced into 135M Env resulting in a 135M (K/EK/N) mutant, and the effect on neutralization by 53M was examined. As shown in FIG. 5, mutating these four residues in the autologous 135M Env resulted in sensitization to 53M serum. Whereas the parental virus was not neutralized at serum dilutions of 1:100 or 1:20, the mutant was neutralized by 53M serum at a dilution of 1:880. This titer was within 2-fold of that of the corresponding titer for the p1666 chimeric Env (Table 3), which contained the complete 53M gp41 sequence in the 133M backbone (see FIG. 1), and the slightly reduced activity may reflect a minor effect on the affinity for the epitope, or may be due to partial masking effects in the chimeric Env. This indicates that introducing these four residues allowed significant expression of the gp41 epitope responsible for neutralization of p1666 Env by 53M serum.

TABLE 3

| Env | Sequence | SEQ ID NO: | 53M Serum* |
|---|---|---|---|
| 135 M | NYT<u>D</u>TIYKLL<u>TE</u>SQSQQDK | 51 | <100 |
| 135 K/EK/N | NYT<u>K</u>TIYKLL<u>EK</u>SQNQQDK | 52 | 880 |
| P1666 (133 M + 53M gp41) | NYT<u>K</u>TIYKLL<u>EK</u>SQNQQEE | 19 | 1650 |

*50% neutralization end-points for the 135M wild-type and mutant Envs are indicated, and compared to the activity against the p1666 chimera that expresses the complete 53M gp41 sequence in the 133M backbone.

Figure 6:
FIG. 6 is the sequence of the region in gp41 of a clade C primary Env (53M; SEQ ID NO:17) that indicates positions of MDER and MPER, including core 2F5 and 4E10 epitopes.

The ability of these mutations to modulate the neutralizing activities of 53M and 135M sera indicates that this region of HR2 is exposed on the surface of intact virions and contains epitopes that can mediate neutralization. The linear relationship of this region to the MPER is indicated in FIG. 6 for the 53M and 135M sequences. To highlight the proximity of this region to the adjacent MPER epitopes, and to distinguish it from the MPER, this region is referred to herein as MDER (Membrane Distal External Region).

These results demonstrate the importance of Lys640 for the 53M MDER epitope. The results in FIG. 5, showing the ability to sensitize the 135M Env to 53M serum by changing just four residues in this region, indicate that any other positions that may be required for expression of this epitope were conserved between these two sequences. This indicates either that the epitope is completely localized to the MDER sequence, or if it requires additional sequences, these are relatively conserved. These properties suggest that this region can be used as a neutralization target.

Example 4

Fusion Proteins that Contain Regions of 53M Env

The analyses of the effect of domain exchanges on neutralization sensitivity showed that neutralization targets were distributed in at least three distinct domains of the 53M Env. Mutagenesis experiments allowed the localization of sequences in gp41 required for neutralization, and related approaches will allow the definition of sequences involved in expression of epitopes in the other domains. A more precise definition of the neutralization targets expressed in these regions and a determination of the structures required to express these epitopes was investigated. This is particularly important in order to distinguish localized epitopes, such as those in V3, from discontinuous, epitopes, such as those in the CD4-bd, and quaternary epitopes, such as the V2-V3 epitope recognized by the 2909 monoclonal antibodies. To accomplish this, the ability of various soluble fusion proteins that contain different Env structures were developed to block or adsorb the neutralizing activity of a particular serum. A positive adsorption result would indicate that the sequence correctly expresses the critical epitope, whereas a lack of adsorption would indicate either that the antibodies being removed are not those mediating neutralization, or the incorrect expression of the epitope in question. It would also be possible to recover the adsorbed antibodies and directly measure their neutralization specificities and potencies.

Thus, soluble fusion proteins were generated that contained various Env regions fused at the N-terminus to a rabbit Fc sequence. For this purpose, the pFUSE vectors (Invivogen, San Diego, Calif.) were utilized. These contain the hEF1-HTLV promoter joined to the IL2 signal sequence, followed by a multi-linker site, followed by the Fc sequence. This system has been successfully used to express a number of wild-type and variant V3 sequences by inserting the relevant coding sequences in-frame between the signal sequence and Fc sequence for both the rabbit and human Fc proteins, with efficient production of secreted proteins in each case.

A series of 53M Env fragments were generated using this system. The regions expressed included the complete V1/V2 domain, several forms of the V1 domain (linear and disulfide-bonded), the V3-V3' domain, the conformational V4 domain and the V5 domain. This system was also used to express several forms of the TM protein, including a large fragment of gp41 that included most of the ectodomain, and two smaller gp41 fragments that contained either the complete 55-residue HR2 region (amino acid residues 622-676) or a smaller 19-residue fragment of HR2 that included the MDER (amino acid residues 633-651). These proteins were readily produced by transfection of 293 cells with the respective fusion vectors, and secreted fusion proteins could either be captured on ELISA plates with a goat-anti-rabbit Fc monoclonal antibody or directly purified on Protein A affinity columns.

Figure 7A:
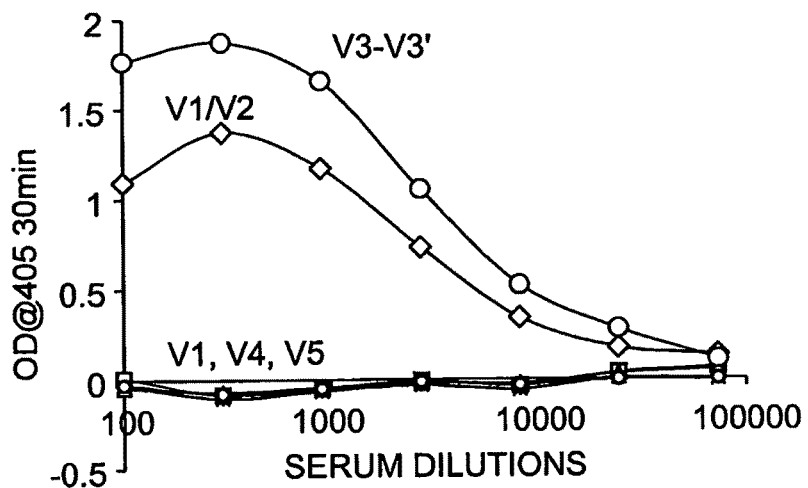
FIG. 7 shows the results of ELISAs performed with 53M serum against fusion proteins expressing the indicated regions of 53M gp120 (FIG. 7A) and gp41 (FIG. 7B).

Using these fusion proteins, it was found that 53M serum contained antibodies capable of binding to the intact V1/V2 domain, the V3-V3' domain, and to all three of the gp41 constructs (FIG. 7A). Antibody activity was not detected against several forms of V1, or to the isolated V4 or V5 proteins. This lack of immunoreactivity of the V1, V4 or V5 domains indicated that these regions were not by themselves neutralization targets or that the fusion protein did not correctly present epitopes present in these domains. The detection of antibodies to V1/V2 and V3-V3' raised the possibility these antibodies may be involved in the neutralization activity specific for the N-terminal and C-terminal halves of gp120. These studies did not rule out the potential role of additional sequences, including complex epitopes involving combinations of domains, as neutralization targets.

Figure 7B:
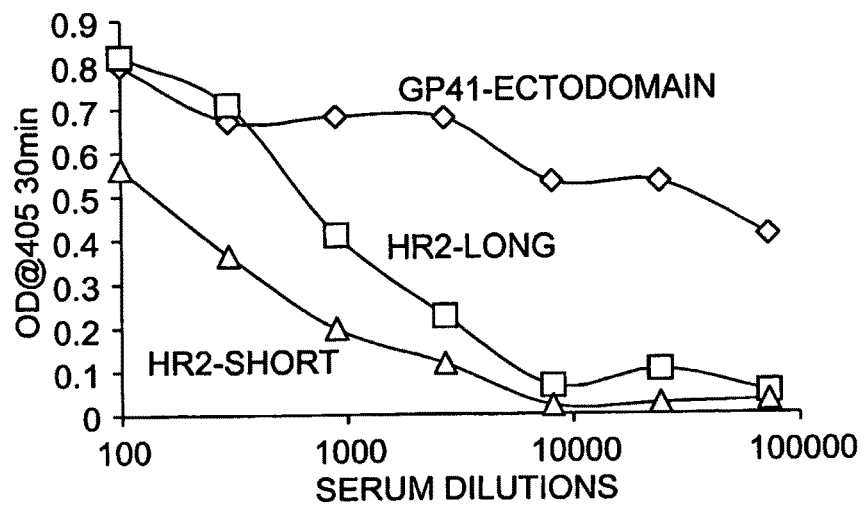

All three gp41-derived fusion proteins were recognized by 53M serum. The full-length protein gave the highest titer, with a 50% point approaching a dilution of 1:100,000. This was despite the fact that this protein was poorly secreted, and was present in the supernatant medium at much lower concentrations than the other proteins. The high titer for this antigen was consistent with the presence of multiple epitopes, including highly immunogenic conserved epitopes in the region between the two heptad repeat regions, HR1 and HR2, which are not believed to possess neutralizing properties. The titer against the large HR2 protein was higher than against the smaller protein (FIG. 7B), indicating either that the full-length sequence contained multiple epitopes (see FIG. 8), or that the affinity of the antibodies was higher for the form of the epitope expressed in the larger HR2 protein, perhaps due to a dependence on additional C-terminal residues that contributed to the affinity of the antibodies.

Example 5

Immunization of Primates

Rhesus macaques provide an animal model suitable for testing of HIV vaccines. In order to determine whether a primate will produce useful neutralizing antibodies when immunized with an MDER peptide, rhesus macaques are immunized with one or more MDER peptides or a control immunogen. The immunogens are formulated with Ribi RAS adjuvant and administered by subcutaneous injection at an initial dose of 25 µg/kg, followed by a boost after 1 month at a dose of 5 µg/kg. Bleeds are taken on the day of and one week after the initial immunization and at weekly intervals following the boost. Antibodies reactive with the immunogen are detected after the first boost. The animal immunized with the control will produce antibodies specific for the control protein, while the animals immunized with the one or more MDER peptides will produce antibodies directed against the MDER peptides.

These antibodies are further characterized by ELISA against one or more MDER peptides. Moreover, reactivity against heterologous peptides, e.g., from the 135M or 133M sequences, can be evaluated to determine the level of cross-reactivity of these antibodies.

What is claimed is:

1. An isolated monoclonal antibody which specifically binds an epitope present on a peptide consisting of the sequence Asn-Tyr-Thr-$Xaa_1$-$Xaa_2$-Ile-Tyr-$Xaa_3$-Leu-$Xaa_4$-Glu-$Xaa_5$-Ser-Gln-Asn-Gln-Gln-Glu-$Xaa_6$-Asn-Glu-$Xaa_7$ (SEQ ID NO:26), wherein $Xaa_1$ is Asp or Asn; $Xaa_2$ is Thr or Leu; $Xaa_3$ is Lys, Arg, or Thr; $Xaa_4$ is Leu or Ile; $Xaa_5$ is Lys, Asp, Glu; $Xaa_6$ is Glu or Lys; and $Xaa_7$ is Lys or Gln.

2. The isolated monoclonal antibody of claim 1, wherein said antibody neutralizes at least one HIV-1 primary isolate.

3. The isolated monoclonal antibody of claim 2, wherein said HIV-1 primary isolate is from clade A, clade B, clade C, clade D, or clade E.

* * * * *